United States Patent
Zhang et al.

(10) Patent No.: US 11,878,290 B2
(45) Date of Patent: Jan. 23, 2024

(54) METHOD FOR REDUCING CARBON DEPOSITS ON CATALYST IN RECYCLING HFC-23

(71) Applicants: Zhejiang Research Institute of Chemical Industry Co., Ltd., Zhejiang (CN); Zhejiang Lantian Environmental Protection Hi-Tech Co., Ltd., Hangzhou (CN); Sinochem Lantian Co., Ltd., Hangzhou (CN)

(72) Inventors: Jianjun Zhang, Zhejiang (CN); Wenfeng Han, Zhejiang (CN); Shucheng Wang, Zhejiang (CN); Wucan Liu, Zhejiang (CN); Feixiang Zhou, Zhejiang (CN)

(73) Assignees: SINOCHEM LANTIAN CO., LTD., Zhejiang (CN); ZHEJIANG LANTIAN ENVIRONMENTAL PROTECTION HI-TECH CO., LTD., Hangzhou (CN); ZHEJIANG RESEARCH INSTITUTE OF CHEMICAL INDUSTRY CO., LTD., Zhejiang (CN)

( * ) Notice: Subject to any disclaimer, the term of this patent is extended or adjusted under 35 U.S.C. 154(b) by 297 days.

(21) Appl. No.: 17/427,554

(22) PCT Filed: Feb. 24, 2020

(86) PCT No.: PCT/CN2020/076371
§ 371 (c)(1),
(2) Date: Jul. 30, 2021

(87) PCT Pub. No.: WO2021/114480
PCT Pub. Date: Jun. 17, 2021

(65) Prior Publication Data
US 2022/0097030 A1    Mar. 31, 2022

(30) Foreign Application Priority Data

Dec. 13, 2019    (CN) .......................... 201911282758.8

(51) Int. Cl.
*B01J 27/13* (2006.01)
*B01J 27/132* (2006.01)
*B01J 37/26* (2006.01)
*C07C 17/20* (2006.01)

(52) U.S. Cl.
CPC ............. *B01J 27/132* (2013.01); *B01J 27/13* (2013.01); *B01J 37/26* (2013.01); *C07C 17/202* (2013.01); *C07C 17/204* (2013.01); *C07C 17/206* (2013.01)

(58) Field of Classification Search
CPC ... C07C 17/202; C07C 17/204; C07C 17/206; B01J 38/10; B01J 35/0013; B01J 37/22; B01J 37/24; B01J 37/26; B01J 27/13; B01J 27/132; B01J 27/12; B01J 23/42; B01J 23/44; B01J 23/462; B01J 23/6522; B01J 23/8993
USPC ................................ 502/228, 229, 230, 326
See application file for complete search history.

(56) References Cited

U.S. PATENT DOCUMENTS

| | | | |
|---|---|---|---|
| 3,009,966 A | 11/1961 | Hauptschein | |
| 2003/0166981 A1* | 9/2003 | Gelblum | C07C 17/269 570/171 |

FOREIGN PATENT DOCUMENTS

| | | |
|---|---|---|
| CN | 104628513 A | 5/2015 |
| CN | 104628514 A | 5/2015 |
| CN | 107162871 A | 9/2017 |
| CN | 107216233 A | 9/2017 |
| CN | 109261142 A | 1/2019 |
| CN | 109748775 A | 5/2019 |
| CN | 109748776 A | 5/2019 |
| WO | WO9629296 A1 | 9/1996 |
| WO | WO03051802 A1 | 6/2003 |

* cited by examiner

*Primary Examiner* — Elizabeth D Wood
(74) *Attorney, Agent, or Firm* — Muncy, Geissler, Olds & Lowe, P.C.

(57) ABSTRACT

Disclosed is a method for reducing carbon deposits on a catalyst in recycling HFC-23. The recycling is realized by means of a fluorine-chlorine exchange reaction with HFC-23 and a halogenated hydrocarbon. The catalyst for the fluorine-chlorine exchange reaction comprises a main body catalyst and a precious metal. The precious metal is selected from at least one of Pt, Pd, Ru, Au or Rh, and has an addition amount of 0.01-2 wt %. During the fluorine-chlorine exchange reaction, hydrogen gas is introduced. The invention has advantages of good catalyst stability, long life, etc.

10 Claims, No Drawings

METHOD FOR REDUCING CARBON DEPOSITS ON CATALYST IN RECYCLING HFC-23

TECHNICAL FIELD

The present invention relates to HFC-23 recycling, particularly to a method for reducing carbon deposits on a catalyst surface and improving the catalyst stability in recycling HFC-23.

BACKGROUND

HFC-23 ($CHF_3$, trifluoromethane, R23) is an inevitable by-product in the industrial production of HFC-22 (HCFC-22, monochlorodifluoromethane, R22 or $CHClF_2$), has a strong greenhouse effect, with a Global Warming Potential (GWP) value of 14,800 times that of $CO_2$. According to statistics, in 2013, HFC-23 emissions in China accounted for 68% of the world's emissions, with a production volume of more than 20,000 tons, equivalent to an annual $CO_2$ emission of 296 million tons. Therefore, HFC-23 recycling is an important issue in realizing energy saving and emission reduction.

At present, HFC-23, a by-product produced in the production process of HCFC-22, is generally discharged directly or disposed by high-temperature incineration at 1200° C. However, direct discharge will cause environmental pollution, and high-temperature incineration at 1200° C. will require high operation and equipment cost, which will increase the production cost of HCFC-22. In view of this, in the prior art, the following methods are adopted for the recycling of HFC-23.

U.S. Pat. No. 3,009,966A discloses a method for preparing TFE and hexafluoropropylene (HFP) by pyrolysis of trifluoromethane at 700-1090° C. However, this method produces more by-product perfluoroisobutylene (PFIB); even at the cost of lowering the yield, a non-negligible amount of PFIB will be produced at a low temperature, while PFIB has extremely high toxicity and its treatment process is more complicated.

WO96/29296A discloses a method for co-cracking HCFC-22 and HFC-23 to form macromolecular fluoroalkanes. Although the conversion rate of HCFC-22 can reach 100% in this method, the yield of the product pentafluoroethane is only 60%, and additional low-value by-products that need treatment or disposal are produced.

U.S. patent US2003/0166981 discloses that HFC-23 and HCFC-22 are pyrolyzed to produce a mixture of pentafluoroethane (HFC-125), heptafluoropropane (HFC-227ea), TFE and HFP at a temperature of 690-775° C. using gold as a catalyst. However, this method has a high pyrolysis temperature and harsh reaction conditions.

Chinese patent CN104628514A discloses that methane and trifluoromethane are introduced into a reactor equipped with a catalyst at a certain ratio, and 02 is added at the same time to react under higher temperature conditions, to generate vinylidene fluoride (VDF). However, this route is also a cracking route, with high pyrolysis temperature and harsh reaction conditions.

Chinese patent CN104628513A discloses a method for converting trifluoromethane and chloroform as raw materials into HCFC-22 under the catalysis of Lewis acid. This method realizes the conversion of trifluoromethane at a relatively low temperature (below 400° C.) through intermolecular fluorine-chlorine exchange. However, this method uses a strong Lewis acid catalyst, which has poor stability and is very prone to deactivation due to carbon deposition and sintering.

Chinese patent CN109748775A discloses that, in the presence of $MgF_2$, $Al_2O_3$, partially fluorinated alumina or $AlF_3$ catalysts, trifluoromethane and dichloromethane are reacted and converted into difluoromethane with a higher value, and at the same time, $Cl_2$, $CCl_4$, $H_2$, $O_2$, $CO_2$, $O_3$ and nitrogen oxide promoting gas are continuously added in the reaction stage, to enhance the catalytic efficiency and stability of the catalyst. However, in this method, the selectivity of the by-product CFC-12 is greatly increased, reaching 2% to 8%, while the product selectivity is low.

SUMMARY

In order to solve the foregoing technical problems, the present invention provides a method for reducing the carbon deposit on a catalyst and improving the stability and life of the catalyst.

The object of the present invention is achieved through the following technical solutions:

A method for improving the stability of catalyst in recycling HFC-23, the recycling is realized by means of a fluorine-chlorine exchange reaction with HFC-23 and a halogenated hydrocarbon:

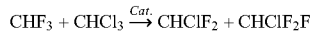

The above fluorine-chlorine exchange products include monochlorodifluoromethane (HCFC-22) and dichlorofluoromethane (HCFC-21). The inventors found that the two products are prone to disproportionation reactions on the surface of the catalyst, causing carbon deposit on the catalyst. The reaction formula is as follows:

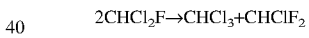

In order to remove carbon deposits on the surface of catalyst, the following technical solutions are adopted.

The catalyst for the fluorine-chlorine exchange reaction comprises a main body catalyst and a precious metal, the precious metal is selected from at least one of Pt, Pd, Ru, Au or Rh, and has an addition amount of 0.01-2 wt %; preferably, the precious metal is Pt or Pd, and has an addition amount of 0.1-0.5 wt %.

During the fluorine-chlorine exchange reaction, hydrogen gas is introduced. The way of introduction: hydrogen gas, HFC-23, and halogenated hydrocarbons form a mixed gas before introducing to a catalyst bed continuously, and the molar ratio of HFC-23, halogenated hydrocarbon and hydrogen is 1:1-3:0.01-0.5. Preferably, the molar ratio of HFC-23, halogenated hydrocarbon and hydrogen is 1:1.5-2.5:0.05-0.2.

Adding precious metal to the main body catalyst can effectively adsorb $H_2$ and realize in-situ hydrogenation of carbon deposits into $CH_4$.

Through the introduction of the precious metal, carbon deposits can be converted, but the generation of carbon deposits cannot be suppressed. In order to achieve rapid desorption of the products HCFC-22 and HCFC-21 on the catalyst surface, fundamentally reduce the carbon deposits on the catalyst surface and improve the stability and life of the catalyst, the following technical solutions are further adopted.

The catalyst further comprises a metal oxide, and the metal oxide is selected at least one metal oxide of K, Na, Fe, Co, Cu, Ni, Zn or Ti, and has an addition amount of 0.1-5 wt %. The addition method is a conventional method for preparing the existing catalyst, such as, physical grinding with the main body catalyst, or incorporation by the metal salt solution precursor wet mixing method or dipping method and then calcination. Preferably, the metal oxide is selected from a metal oxide of Fe, Co, Ni or Zn, and has an addition amount of 0.5-2 wt %.

The main body catalyst is a chromium, aluminum, magnesium-based catalyst or a chromium, aluminum, or magnesium catalyst supported on activated carbon/graphite; preferably, the main body catalyst is selected from at least one of $Cr_2O_3$, $Cr_2O_3/Al_2O_3$, $Cr_2O_3/AlF_3$, $Cr_2O_3/C$, MgO, $MgO/Al_2O_3$, $MgO/AlF_3$, $MgO/AlF_3$, $Al_2O_3$ or $AlF_3$.

The catalyst of the present invention needs to be pretreated. When the catalyst comprises a main body catalyst and a precious metal, the precious metal is added after pretreatment of the main body catalyst; and when the catalyst comprises a main body catalyst, a precious metal and a metal oxide, the pretreatment is performed after the metal oxide is added to the main body catalyst, and the precious metal is added after pretreatment. The pretreatment process comprises the following steps:
(1) Performing fluorination treatment at 250° C.-450° C. for 1-6 h under a mixed atmosphere of 1%-20% hydrogen fluoride and 80%-99% nitrogen;
(2) Performing treatment at 300° C.-500° C. for 2-8 h under hydrogen fluoride atmosphere;
(3) Introducing nitrogen gas for purging and cooling.

The halogenated hydrocarbon in the fluorine-chlorine exchange reaction is chloroform or a mixture containing chloroform. The conditions for the fluorine-chlorine exchange reaction are: a molar ratio of HFC-23 to halogenated hydrocarbon of 1:1-3, a reaction temperature of 250-400° C., a reaction pressure of 0.1-3 bar, and a residence time of 4-50s. Preferably, a molar ratio of HFC-23 to halogenated hydrocarbon of 1:1-2, a reaction temperature of 300-360° C., a reaction pressure of 0.1-2 bar, and a residence time of 4-12s.

Compared with the prior art, the present invention has the following beneficial effects.
(1) In the present invention, by adding precious metal to the main body catalyst, and continuously introducing the mixture of hydrogen gas and raw material gas (HFC-23 and halogenated hydrocarbon) during the fluorine-chlorine exchange reaction into the catalyst bed to promote the adsorption of hydrogen gas on the catalyst surface and promote the in-situ hydrogenation of carbon on the catalyst surface to generate $CH_4$, the carbon deposit on the catalyst is eliminated in-situ and the stability and life of the catalyst is improved. In addition, because HFC-23, halogenated hydrocarbon (chloroform), HCFC-22 and HCFC-21 in the reaction system can be used as fire extinguishing agent or refrigerant and the combustion performance is poor, the suppression of carbon deposit on the catalyst using highly reactive hydrogen has less impact on the target reaction performance, and the selective elimination of carbon deposits can be realized;
(2) By adding metal oxide to the catalyst, the present invention accelerates the desorption of the products HCFC-22 and HCFC-21 on the surface of the catalyst, thereby inhibiting the disproportionation reaction on the surface of the catalyst, reducing the carbon deposition caused by side reactions and improving the stability and life of the catalyst;
(3) By adding precious metal and metal oxide to the main body catalyst at the same time, the present invention can not only inhibit the generation of carbon deposits, but also eliminate the carbon deposits in situ, exert a better synergistic effect, and significantly improve the stability and extend the life of the catalyst.

SUMMARY

The present invention will be further described below in conjunction with specific examples, but the present invention is not limited to these specific embodiments. Those skilled in the art should realize that the present invention covers all alternatives, improvements and equivalents that may be included in the scope of the claims.

EXAMPLE 1

Preparation of catalyst: The pretreatment of chromium trioxide (main body catalyst) was performed. The pretreatment process comprised: 1) performing fluorination treatment at 250° C. for 2 h under a mixed atmosphere of 10% hydrogen fluoride and 90% nitrogen; 2) performing treatment at 300° C. for 5 h under hydrogen fluoride atmosphere; 3) introducing nitrogen gas for purging and cooling. The catalyst after fluorination pretreatment was poured into n-hexane and stirred to disperse evenly, then Ru nano colloidal dispersion was added dropwise to control the Ru loading mass content to 0.1%. After stirring continuously for 4 h and standing, the upper layer of the solution became transparent and clear and was transferred to a rotary evaporator for rotary drying at 80° C., and dried overnight at 110° C. in an oven, calcined in a muffle furnace at 400° C. for 6 hours to obtain a formed catalyst, which was designated as catalyst 1.

HFC-23 recycling: Trifluoromethane, chloroform and hydrogen gas were introduced into a reactor containing 50 ml of catalyst 1 at a molar ratio of 1:1.5:0.2, and a fluorine-chlorine exchange reaction was carried out under the conditions of a reaction temperature of 310° C., a pressure of 1 bar and a residence time of 5s. The conversion rate of trifluoromethane was 27.1%, the selectivity of HCFC-22 was 45.7%, and the selectivity of HCFC-21 was 53.1%. The tail gas contained a small amount of by-product gases such as CFC-12 and trace amount of methane. The catalyst was significantly deactivated after 905 h, indicating that a precious metal Ru catalyst with hydrogenation performance was loaded and the introduction of hydrogen gas could eliminate the carbon deposits, to achieve in-situ regeneration of the catalyst.

EXAMPLE 2

Preparation of catalyst: The pretreatment of chromium trioxide (main body catalyst) was performed. The pretreatment process comprised: 1) performing fluorination treatment at 250° C. for 2 h under a mixed atmosphere of 10% hydrogen fluoride and 90% nitrogen; 2) performing treatment at 300° C. for 5 h under hydrogen fluoride atmosphere; 3) introducing nitrogen gas for purging and cooling. The catalyst after fluorination pretreatment was poured into n-hexane and stirred to disperse evenly, then Pt nano colloidal dispersion was added dropwise to control the Pt loading mass content to 0.1%. After stirring continuously for 4 h and standing, the upper layer of the solution became transparent and clear and was transferred to a rotary evaporator for rotary drying at 80° C., and dried overnight at 110° C. in an oven, calcined in a muffle furnace at 400° C. for 6 hours to obtain a formed catalyst, which was designated as catalyst 2.

HFC-23 recycling: Trifluoromethane, chloroform and hydrogen gas were introduced into a reactor containing 50 ml of catalyst 2 at a molar ratio of 1:1.5:0.2, and a fluorine-chlorine exchange reaction was carried out under the conditions of a reaction temperature of 310° C., a pressure of 1 bar and a residence time of 5s. The conversion rate of trifluoromethane was 27.9%, the selectivity of HCFC-22 was 45.9%, and the selectivity of HCFC-21 was 52.9%. The tail gas contained a small amount of by-product gases such as CFC-12 and trace amount of methane. The catalyst was significantly deactivated after 989 h, indicating that a precious metal Pt catalyst with hydrogenation performance was loaded and the introduction of hydrogen gas could eliminate the carbon deposits, to achieve in-situ regeneration of the catalyst.

EXAMPLE 3

Preparation of catalyst: The pretreatment of chromium trioxide (main body catalyst) was performed. The pretreatment process comprised: 1) performing fluorination treatment at 250° C. for 2 h under a mixed atmosphere of 10% hydrogen fluoride and 90% nitrogen; 2) performing treatment at 300° C. for 5 h under hydrogen fluoride atmosphere; 3) introducing nitrogen gas for purging and cooling. The catalyst after fluorination pretreatment was poured into n-hexane and stirred to disperse evenly, then Pd nano colloidal dispersion was added dropwise to control the Pd loading mass content to 0.1%. After stirring continuously for 4 h and standing, the upper layer of the solution became transparent and clear and was transferred to a rotary evaporator for rotary drying at 80° C., and dried overnight at 110° C. in an oven, calcined in a muffle furnace at 400° C. for 6 hours to obtain a formed catalyst, which was designated as catalyst 3.

HFC-23 recycling: Trifluoromethane, chloroform and hydrogen gas were introduced into a reactor containing 50 ml of catalyst 3 at a molar ratio of 1:1.5:0.2, and a fluorine-chlorine exchange reaction was carried out under the conditions of a reaction temperature of 310° C., a pressure of 1 bar and a residence time of 5s. The conversion rate of trifluoromethane was 26.9%, the selectivity of HCFC-22 was 43.9%, and the selectivity of HCFC-21 was 54.7%. The tail gas contained a small amount of by-product gases such as CFC-12 and trace amount of methane. The catalyst was significantly deactivated after 956 h, indicating that a precious metal Pd catalyst with hydrogenation performance was loaded and the introduction of hydrogen gas could eliminate the carbon deposits, to achieve in-situ regeneration of the catalyst.

EXAMPLE 4

The operation procedure of this embodiment was the same as that of Example 2, except for the difference that the main body catalyst chromium trioxide of Example 2 was replaced with $AlF_3$, and the prepared catalyst was designated as catalyst 4.

The conversion rate of trifluoromethane was 26.8%, the selectivity of HCFC-22 was and the selectivity of HCFC-21 was 53.9%. The tail gas contained a small amount of by-product gases such as CFC-12 and trace amount of methane. The catalyst was significantly deactivated after 978 h, indicating that a precious metal Pt catalyst with hydrogenation performance was loaded onto the $AlF_3$ main body catalyst, and the introduction of hydrogen gas could in-situ eliminate the carbon deposits, to achieve regeneration of the catalyst.

EXAMPLE 5

The operation procedure of this embodiment was the same as that of Example 2, except for the difference that the Pt loading in Example 2 was dropped from 0.1 wt % to 0.05 wt %, and the prepared catalyst was designated as catalyst 5.

The conversion rate of trifluoromethane was 27.0%, the selectivity of HCFC-22 was and the selectivity of HCFC-21 was 53.1%. The tail gas contained a small amount of by-product gases such as CFC-12 and trace amount of methane. The catalyst was significantly deactivated after 817 h. Compared with the results of Example 2, it indicated that the loading of the hydrogenated precious metal catalyst was reduced to 0.05 wt %, and the ability to in-situ eliminate carbon deposits was decreased.

EXAMPLE 6

The operation procedure of this embodiment was the same as that of Example 2, except for the difference that the Pt loading in Example 2 was increased from 0.1 wt % to 1.0 wt %, and the prepared catalyst was designated as catalyst 6.

The conversion rate of trifluoromethane was 26.8%, the selectivity of HCFC-22 was and the selectivity of HCFC-21 was 53.2%. The tail gas contained a small amount of by-product gases such as CFC-12 and trace amount of methane. The catalyst was significantly deactivated after 854h. Compared with the results of Example 2, it indicated that when the loading of the hydrogenated precious metal catalyst was increased to 1.0 wt %, and the ability to in-situ eliminate carbon deposits was decreased.

EXAMPLE 7

Preparation of catalyst: Chromium trioxide (main body catalyst) and cobalt trioxide powder were ground and mixed, and the mass content of Co was controlled to 1.0% to obtain 1.0% $Co/Cr_2O_3$ catalyst precursor. The pretreatment of the 1.0% $Co/Cr_2O_3$ catalyst precursor was performed. The pretreatment process comprised: 1) performing fluorination treatment at 250° C. for 2 h under a mixed atmosphere of 10% hydrogen fluoride and 90% nitrogen; 2) performing treatment at 300° C. for 5 h under hydrogen fluoride atmosphere; 3) introducing nitrogen gas for purging and cooling.

The catalyst after fluorination pretreatment was poured into n-hexane and stirred to disperse evenly, then Pt nano colloidal dispersion was added dropwise to control the Pt loading mass content to 0.1%. After stirring continuously for 4 h and standing, the upper layer of the solution became transparent and clear and was transferred to a rotary evaporator for rotary drying at 80° C., and dried overnight at 110° C. in an oven overnight, calcined in a muffle furnace at 400° C. for 6 hours to obtain a formed catalyst, which was designated as catalyst 7.

HFC-23 recycling: Trifluoromethane, chloroform and hydrogen gas were introduced into a reactor containing 50 ml of catalyst 7 at a molar ratio of 1:1.5:0.1, and a fluorine-chlorine exchange reaction was carried out under the conditions of a reaction temperature of 310° C., a reaction pressure of 1 bar and a residence time of 5s. The conversion rate of trifluoromethane was 26.7%, the selectivity of HCFC-22 was 48.6%, and the selectivity of HCFC-21 was 50.3%. The tail gas contained a small amount of by-product gases such as CFC-12 and trace amount of methane. The catalyst was significantly deactivated after 2063 h, indicating that the chromium trioxide main body catalyst has a synergistic effect when supporting precious metal Pt with hydrogenation performance and Co to avoid carbon deposition. The life of the catalyst was longer than that under the situations with a single addition of precious metals or a single addition of metal oxides.

EXAMPLE 8

Preparation of catalyst: Aluminium fluoride (main body catalyst) and cobalt trioxide powder were ground and mixed, and the mass content of Co was controlled to 1.0% to obtain 1.0% Co/AlF$_3$ catalyst precursor. The pretreatment of the 1.0% Co/AlF$_3$ catalyst precursor was performed. The pretreatment process comprised: 1) performing fluorination treatment at 250° C. for 2 h under a mixed atmosphere of 10% hydrogen fluoride and 90% nitrogen; 2) performing treatment at 300° C. for 5 h under hydrogen fluoride atmosphere; 3) introducing nitrogen gas for purging and cooling.

The catalyst after fluorination pretreatment was poured into n-hexane and stirred to disperse evenly, then Pt nano colloidal dispersion was added dropwise to control the Pt loading mass content to 0.1%. After stirring continuously for 4 h and standing, the upper layer of the solution became transparent and clear and was transferred to a rotary evaporator for rotary drying at 80° C., and dried overnight at 110° C. in an oven overnight, calcined in a muffle furnace at 400° C. for 6 hours to obtain a formed catalyst, which was designated as catalyst 8.

HFC-23 recycling: Trifluoromethane, chloroform and hydrogen gas were introduced into a reactor containing 50 ml of catalyst 8 at a molar ratio of 1:1.5:0.2, and a fluorine-chlorine exchange reaction was carried out under the conditions of a reaction temperature of 310° C., a reaction pressure of 1 bar and a residence time of 5s. The conversion rate of trifluoromethane was 26.7%, the selectivity of HCFC-22 was 44.6%, and the selectivity of HCFC-21 was 54.3%. The tail gas contained a small amount of by-product gases such as CFC-12 and trace amount of methane. The catalyst was significantly deactivated after 2145 h, indicating that the aluminum fluoride main body catalyst has a synergistic effect when supporting precious metal Pt with hydrogenation performance and Co to avoid carbon deposition. The life of the catalyst was longer than that under the situations with a single addition of precious metals or a single addition of metal oxides.

COMPARATIVE EXAMPLE 1

The pretreatment of chromium trioxide catalyst was performed. The pretreatment process comprised: 1) performing fluorination treatment at 250° C. for 2 h under a mixed atmosphere of 10% hydrogen fluoride and 90% nitrogen; 2) performing treatment at 300° C. for 5 h under hydrogen fluoride atmosphere; 3) introducing nitrogen gas for purging and cooling. The catalyst after pretreatment was designated as B1.

HFC-23 recycling: Trifluoromethane and chloroform were introduced into a reactor containing 50 ml of catalyst B1 at a molar ratio of 1:1.5, and a fluorine-chlorine exchange reaction was carried out under the conditions of a reaction temperature of 310° C., a pressure of 1 bar and a residence time of 5s. The conversion rate of trifluoromethane was 25.6%, the selectivity of HCFC-22 was 44.4%, and the selectivity of HCFC-21 was 55.2%. The tail gas contained a small amount of by-product gases such as CFC-12. The catalyst was significantly deactivated after 340 h. The catalyst was taken out and found to be obviously blackened with serious carbon deposits.

COMPARATIVE EXAMPLE 2

The operation procedure of this Comparative Example is the same as that of Comparative Example 1, except for the difference that, the catalyst chromium trioxide was replaced with AlF3 and the catalyst after pretreatment was designated as B2.

The conversion rate of trifluoromethane was 25.8%, the selectivity of HCFC-22 was 44.2%, and the selectivity of HCFC-21 was 54.9%. The tail gas contained a small amount of by-product gases such as CFC-12. The catalyst was significantly deactivated after 395 h. The catalyst was taken out and found to be obviously blackened with serious carbon deposits.

COMPARATIVE EXAMPLE 3

Preparation of catalyst: The pretreatment of chromium trioxide (main body catalyst) was performed. The pretreatment process comprised: 1) performing fluorination treatment at 250° C. for 2 h under a mixed atmosphere of 10% hydrogen fluoride and 90% nitrogen; 2) performing treatment at 300° C. for 5 h under hydrogen fluoride atmosphere; 3) introducing nitrogen gas for purging and cooling. The catalyst after fluorination pretreatment was poured into n-hexane and stirred to disperse evenly, then Ag nano colloidal dispersion was added dropwise to control the Ag loading to 0.1 wt %. After stirring continuously for 4 h and standing, the upper layer of the solution became transparent and clear and was transferred to a rotary evaporator for rotary drying at 80° C., and dried overnight at 110° C. in an oven, calcined in a muffle furnace at 400° C. for 6 hours to obtain a formed catalyst, which was designated as catalyst B3.

HFC-23 recycling: Trifluoromethane, chloroform and hydrogen gas were introduced into a reactor containing 50 ml of catalyst 2 at a molar ratio of 1:1.5:0.2, and a fluorine-chlorine exchange reaction was carried out under the conditions of a reaction temperature of 310° C., a pressure of 1 bar and a residence time of 5s.

The conversion rate of trifluoromethane was 26.3%, the selectivity of HCFC-22 was and the selectivity of HCFC-21 was 53.2%. The tail gas contained a small amount of by-product gases such as CFC-12 and trace amount of methane. The catalyst was significantly deactivated after 321 h, indicating that a precious metal Ag supported on the main body catalyst, and the introduction of hydrogen gas could not achieve in-situ regeneration of the catalyst.

COMPARATIVE EXAMPLE 4

Preparation of catalyst: Chromium trioxide and cobalt trioxide powder were ground and mixed, and the Co mass content was controlled to 1.0% to obtain 1.0% Co/Cr$_2$O$_3$ catalyst precursor. The pretreatment of the 1.0% Co/Cr$_2$O$_3$ catalyst precursor was performed. The pretreatment process comprised: 1) performing fluorination treatment at 250° C. for 2 h under a mixed atmosphere of 10% hydrogen fluoride and 90% nitrogen; 2) performing treatment at 300° C. for 5 h under hydrogen fluoride atmosphere; 3) introducing nitrogen gas for purging and cooling. The catalyst after pretreatment was designated as B4.

HFC-23 recycling: Trifluoromethane and chloroform were introduced into a reactor containing 50 ml of catalyst B4 at a molar ratio of 1:1.5, and a fluorine-chlorine exchange reaction was carried out under the conditions of a reaction temperature of 310° C., a pressure of 1 bar and a residence time of 5s.

The conversion rate of trifluoromethane was 26.6%, the selectivity of HCFC-22 was 44.3%, and the selectivity of HCFC-21 was 54.7%. The tail gas contained a small amount of by-product gases such as CFC-12. The catalyst was significantly deactivated after 973 h. The experimental results showed that the addition of $Co_2O_3$ could effectively improve the stability and life of the catalyst.

COMPARATIVE EXAMPLE 5

Preparation of catalyst: Chromium trioxide and iron trioxide powder were ground and mixed, and the Fe mass content was controlled to 1.0% to obtain 1.0% $Fe/Cr_2O_3$ catalyst precursor. The pretreatment of 1.0% $Fe/Cr_2O_3$ catalyst precursor was performed. The pretreatment process comprised: 1) performing fluorination treatment at 250° C. for 2 h under a mixed atmosphere of 10% hydrogen fluoride and 90% nitrogen; 2) performing treatment at 300° C. for 5 h under hydrogen fluoride atmosphere; 3) introducing nitrogen gas for purging and cooling. The catalyst after pretreatment was designated as B5.

HFC-23 recycling: Trifluoromethane and chloroform were introduced into a reactor containing 50 ml of catalyst B5 at a molar ratio of 1:1.5, and a fluorine-chlorine exchange reaction was carried out under the conditions of a reaction temperature of 310° C., a pressure of 1 bar and a residence time of 5s.

The conversion rate of trifluoromethane was 26.3%, the selectivity of HCFC-22 was 44.7%, and the selectivity of HCFC-21 was 54.4%. The tail gas contained a small amount of by-product gases such as CFC-12. The catalyst was significantly deactivated after 861h. The experimental results showed that the addition of $Fe_2O_3$ could effectively improve the stability and life of the catalyst.

COMPARATIVE EXAMPLE 6

Preparation of catalyst: Chromium trioxide and nickel trioxide powder were ground and mixed, and the Ni mass content was controlled to 1.0% to obtain 1.0% $Ni/Cr_2O_3$ catalyst precursor. The pretreatment of the 1.0% $Ni/Cr_2O_3$ catalyst precursor was performed. The pretreatment process comprised: 1) performing fluorination treatment at 250° C. for 2 h under a mixed atmosphere of 10% hydrogen fluoride and 90% nitrogen; 2) performing treatment at 300° C. for 5 h under hydrogen fluoride atmosphere; 3) introducing nitrogen gas for purging and cooling. The catalyst after pretreatment was designated as B6.

HFC-23 recycling: Trifluoromethane and chloroform were introduced into a reactor containing 50 ml of catalyst B6 at a molar ratio of 1:1.5, and a fluorine-chlorine exchange reaction was carried out under the conditions of a reaction temperature of 310° C., a pressure of 1 bar and a residence time of 5s.

The conversion rate of trifluoromethane was 25.3%, the selectivity of HCFC-22 was 43.7%, and the selectivity of HCFC-21 was 55.4%. The tail gas contained a small amount of by-product gases such as CFC-12. The catalyst was significantly deactivated after 758 h. The experimental results showed that the addition of $Ni_2O_3$ could effectively improve the stability and life of the catalyst.

COMPARATIVE EXAMPLE 7

The operation procedure of this Comparative Example was the same as that of Comparative Example 4, except for the difference that, the catalyst chromium trioxide was replaced with aluminum fluoride, and the catalyst after pretreatment was designated as B7.

The conversion rate of trifluoromethane was 26.3%, the selectivity of HCFC-22 was 44.1%, and the selectivity of HCFC-21 was 54.9%. The tail gas contained a small amount of by-product gases such as CFC-12. The catalyst was significantly deactivated after 965 h. The experimental results showed that the addition of $Co_2O_3$ to the main body catalyst $AlF_3$ could effectively improve the stability and life of the catalyst.

COMPARATIVE EXAMPLE 8

The operation procedure of this Comparative Example was the same as that of Comparative Example 4, except for the difference that, the mass content of Co in Comparative Example 4 was reduced from 1.0% to 0.1%, and the prepared catalyst was designated as B8.

The conversion rate of trifluoromethane was 26.4%, the selectivity of HCFC-22 was 44.1%, and the selectivity of HCFC-21 was 54.9%. The tail gas contained a small amount of by-product gases such as CFC-12. The catalyst was significantly deactivated after 654 h. Compared with Comparative with the Comparative Example 4, the experimental results showed that the ability to improve the stability and life of the catalyst was weakened when the mass content of added $Co_2O_3$ was 0.1%.

COMPARATIVE EXAMPLE 9

The operation procedure of this Comparative Example was the same as that of Comparative Example 4, except for the difference that, the mass content of Co in Comparative Example 4 was increased from 1.0% to 5.0%, and the prepared catalyst was designated as B9.

The conversion rate of trifluoromethane was 26.3%, the selectivity of HCFC-22 was 44.4%, and the selectivity of HCFC-21 was 54.3%. The tail gas contained a small amount of by-product gases such as CFC-12. The catalyst was significantly deactivated after 804h. Compared with Comparative Example 4, the experimental results showed that the ability to improve the stability and life of the catalyst was weakened when the mass content of added $Co_2O_3$ was 5.0%.

TABLE 1

Catalytic effect of different catalyst systems

| No. | Catalyst | Life of catalyst (h) |
|---|---|---|
| Example 1 | 1 | 905 |
| Example 2 | 2 | 989 |
| Example 3 | 3 | 956 |
| Example 4 | 4 | 978 |
| Example 5 | 5 | 817 |
| Example 6 | 6 | 854 |
| Example 7 | 7 | 2063 |
| Example 8 | 8 | 2145 |

TABLE 1-continued

Catalytic effect of different catalyst systems

| No. | Catalyst | Life of catalyst (h) |
|---|---|---|
| Comparative Example 1 | B1 | 340 |
| Comparative Example 2 | B2 | 395 |
| Comparative Example 3 | B3 | 321 |
| Comparative Example 4 | B4 | 973 |
| Comparative Example 5 | B5 | 861 |
| Comparative Example 6 | B6 | 758 |
| Comparative Example 7 | B7 | 965 |
| Comparative Example 8 | B8 | 654 |
| Comparative Example 9 | B9 | 804 |

The invention claimed is:

1. A method for reducing carbon deposits on a catalyst in recycling HFC-23, the recycling is realized by means of a fluorine-chlorine exchange reaction with HFC-23 and a halogenated hydrocarbon, wherein the catalyst for the fluorine-chlorine exchange reaction comprises a main body catalyst and a precious metal, the precious metal is selected from at least one of Pt, Pd, Ru, Au or Rh, and has an addition amount of 0.01-2 wt %;

during the fluorine-chlorine exchange reaction, hydrogen gas is introduced.

2. The method for reducing carbon deposits on a catalyst in recycling HFC-23 according to claim 1, wherein the precious metal is Pt or Pd, and has an addition amount of 0.1-5 wt %.

3. The method for reducing carbon deposits on a catalyst in recycling HFC-23 according to claim 1, wherein the catalyst further comprises a metal oxide, and the metal oxide is selected at least one metal oxide of K, Na, Fe, Co, Cu, Ni, Zn or Ti, and has an addition amount of 0.1-5 wt %.

4. The method for reducing carbon deposits on a catalyst in recycling HFC-23 according to claim 3, wherein the metal oxide is selected from metal oxides of Fe, Co, Ni or Zn, and has an addition amount of 0.5-2 wt %.

5. The method for reducing carbon deposits on a catalyst in recycling HFC-23 according to claim 1, wherein hydrogen gas, HFC-23, and halogenated hydrocarbons form a mixed gas before introduction, and the molar ratio of HFC-23, halogenated hydrocarbon and hydrogen is 1:1-3:0.01-0.5.

6. The method for reducing carbon deposits on a catalyst in recycling HFC-23 according to claim 5, wherein hydrogen gas is continuously introduced into a catalyst bed.

7. The method for reducing carbon deposits on a catalyst in recycling HFC-23 according to claim 3, wherein the catalyst is pretreated, and the pretreatment process comprises the following steps:
 (1) Performing fluorination treatment at 250° C.-450° C. for 1-6 h under a mixed atmosphere of 1%-20% hydrogen fluoride and 80%-99% nitrogen;
 (2) Performing treatment at 300° C.-500° C. for 2-8 h under hydrogen fluoride atmosphere;
 (3) Introducing nitrogen gas for purging and cooling.

8. The method for reducing carbon deposits on a catalyst in recycling HFC-23 according to claim 1, wherein the halogenated hydrocarbon is chloroform or a mixture containing chloroform.

9. The method for reducing carbon deposits on a catalyst in recycling HFC-23 according to claim 8, wherein the main body catalyst is chromium, aluminum, or magnesium-based catalyst or chromium, aluminum, or magnesium catalyst supported on activated carbon/graphite.

10. The method for reducing carbon deposits on a catalyst in recycling HFC-23 according to claim 1, wherein the conditions for the fluorine-chlorine exchange reaction are: a molar ratio of HFC-23 to halogenated hydrocarbon of 1:1-3, a reaction temperature of 250-400° C., a reaction pressure of 0.1-3 bar, and a residence time of 4-50 s.

* * * * *